United States Patent [19]

D'Amico

[11] 4,448,399
[45] May 15, 1984

[54] BENZTHIAZOLYL-2-THIOALKANOIC NITRILES

[75] Inventor: John J. D'Amico, Los Angeles, Calif.

[73] Assignee: Monsanto Company, St. Louis, Mo.

[21] Appl. No.: 254,812

[22] Filed: Apr. 16, 1981

Related U.S. Application Data

[63] Continuation-in-part of Ser. No. 212,389, Dec. 3, 1980, abandoned, which is a continuation of Ser. No. 120,436, Feb. 11, 1980, abandoned, which is a continuation-in-part of Ser. No. 915,846, Jun. 15, 1978, abandoned.

[51] Int. Cl.$^3$ .............................................. C07D 277/74
[52] U.S. Cl. ....................................... 548/165; 71/90; 71/88; 548/173; 548/221
[58] Field of Search ............................................. 548/165

[56] References Cited

U.S. PATENT DOCUMENTS

| | | | |
|---|---|---|---|
| 2,424,175 | 7/1947 | Jones et al. | 548/165 |
| 2,912,357 | 11/1959 | Harman et al. | 548/165 |
| 3,069,429 | 12/1962 | Godson et al. | 548/165 |
| 3,455,676 | 7/1969 | Ayad | 548/165 |
| 4,049,419 | 9/1977 | D'Amico | 548/165 |
| 4,353,916 | 10/1982 | Uematsu | 424/270 |

FOREIGN PATENT DOCUMENTS 118318 8/1942 Australia .............................. 548/165

Primary Examiner—Paul M. Coughlan, Jr.
Assistant Examiner—D. B. Springer
Attorney, Agent, or Firm—Richard H. Shear; Raymond C. Loyer; James C. Bolding

[57] ABSTRACT

The invention relates to compounds having the formula

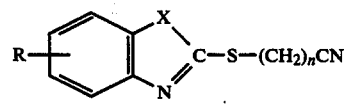

wherein R is equal to hydrogen, halogen or alkyl containing 1-5 carbon atoms; X is equal to oxygen, sulfur or —NH; n is equal to the integer 1 to 6; with the proviso when X is —NH, n may not equal 6. These compounds are useful in regulating the growth of leguminous plants.

6 Claims, No Drawings

BENZTHIAZOLYL-2-THIOALKANOIC NITRILES

This application is a continuation-in-part of application Ser. No. 212,389, filed Dec. 3, 1980, now abandoned which was a continuation of application Ser. No. 120,436 filed Feb. 11, 1980, now abandoned, which was a continuation-in-part of application Ser. No. 915,846, filed June 15, 1978, now abandoned.

This invention relates to certain novel 2-benzothiazolylthioalkanoic nitriles, 2-benzoxazolylthioalkanoic nitriles and 2-benzimidazolylthioalkanoic nitriles and their use to regulate the growth of leguminous plants. More specifically, it relates to compounds having the formula

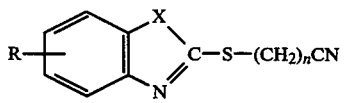

wherein X is equal to oxygen, sulfur or —NH; R is equal to hydrogen, halogen or alkyl containing 1 to 5 carbon atoms; n is the integer 1 to 6; with the proviso when X is —NH, n may not equal 6, as well as to their use in regulating the growth of leguminous plants.

Preferred are those compounds in which R is hydrogen, methyl or chloro and n is 1 to 3, preferably 3.

As used herein, the term "alkyl" means those alkyl groups, branched as well as unbranched, having up to 5 carbon atoms. The term "halogen" refers to chlorine, bromine, iodine and fluorine atoms.

In accordance with the novel aspects of the present invention, the compounds of the foregoing formula are effective plant growth regulants, especially in the regulation of leguminous plants.

The term "plant regulant" or "plant growth regulant," as employed in this application, connotes a material which serves to modify the normal sequential development of a treated plant to agricultural maturity. Such modification may result from the effect of material on the physiological processes of the plant or from the effect of said material on the morphology of the plant. It should additionally be recognized that modifications may also result from a combination or sequence of both physiological and morphological factors.

Modifying effects of a plant regulant are probably most readily observed as changes in the size, shape, color or texture of the treated plant or any of its parts. Similarly, changes in the quantity of the plant fruit or flowers are also quite apparent from simple, visual inspection. The above changes may be characterized as an acceleration or retardation of plant growth, such as an increase or decrease in dry weight accumulation, stature reduction, leaf or canopy alteration, increased branching, terminal inhibition, increased flowering or fruit set.

Modifications in the normal sequential development of a treated plant to agricultural maturity may also be manifested by reduced transpiration or increased carbohydrate deposition or protein content.

It is to be understood that each response may occur in conjunction with other responses, but may occur separately. For example, depending upon various factors realized by those skilled in the art to effect activity, the data illustrated below demonstrates that the compounds of the present invention sometimes alter the leaf morphology even though the plants are not reduced in stature.

Alteration of the leaf morphology of leguminous plants is important because leguminous plants have canopies that effectively inhibit sunlight from reaching the lower leaves. For example, only about 50% of a soybean plant's leaves intercept light for photosynthesis. Approximately 85% of the light is absorbed by the outer layer of leaves. Many researchers feel that by altering the morphology of the leaves such that the canopy is altered, light may fall more deeply into the canopy, and yields could be increased. Weber, in "Field Crop Abstracts," Volume 21, No. 4, pages 313–317, states that "greater light penetration, resulting in greater amount of the [soybean] plant canopy having a light intensity above 150 f.c., generally led to higher seed yields." Johnson et al, in "Crop Science," Volume 9, pages 577–581, states that "adding light increased the yields of bottom, middle and top canopy positions of [soybean] plants 30, 20 and 2%, respectively." Thus, it would be highly beneficial if a method was found whereby the leaves of such plants could be altered such that a greater number of leaves could be illuminated.

Increased plant dry matter accumulation is another valuable plant growth regulant response which can occur in conjunction with morphological changes or can be the sole plant growth response detected. Increased dry matter accumulation is the physically measurable manifestation of increased plant photosynthetic activity. Most plants capture no more than 1 to 3 percent of the solar energy they receive. Present knowledge suggests that it is theoretically possible to increase this rate to approximately twelve percent. Enhancement of photosynthesis at the appropriate stage of the plant's growth and development may enable the plant to fix more carbon dioxide resulting in the production of increased amounts of carbohydrate, amino acids, etc., which could be available for utilization in the plant's reproductive activities, leading to increased crop yields.

The regulation of plants in accordance with the instant invention does not include the total inhibition or the killing of such plants. Although phytotoxic amounts of the materials disclosed herein might be employed to exert a herbicidal (killing) action, it is contemplated herein to employ only plant regulating amounts of such materials in order to modify the normal sequential development of the treated plant to agricultural maturity. The application of a plant regulating amount may be applied to plants in sequence at various stages of the plant's development to obtain various desirable responses. As may be expected, and as is apparent to those skilled in the art, such plant regulating amount will vary, not only with the material selected, but also with the modifying effect desired, the species of plant and its stage of development, the plant growth medium and whether a permanent or transitory effect is sought.

Nitriles of Formula I wherein n is 1 or 3 are prepared by reacting the appropriate 2-mercaptobenzoxazole, 2-mercaptobenzothiazole or 2-mercaptobenzimidazole with potassium hydroxide and chloroacetonitrile, or 4-chlorobutyronitrile in accordance with the following reaction scheme:

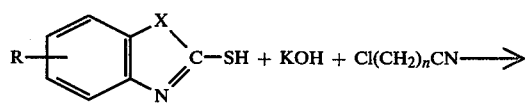

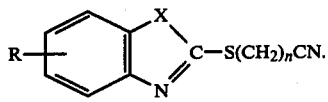

grams (0.2 mole) of potassium hydroxide and 500 ml. of water, 15.2 grams (0.2 mole) of chloroacetonitrile was added in one portion. After stirring at 25°–30° C. for three hours, the solid was collected by filtration, washed with water until neutral to litmus and air-dried at 25°–30° C. The data are summarized in Table I.

TABLE I

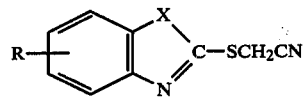

| Compound No. | R | X | m.p. °C. | Percent Yield | Percent C Calc'd. | Percent C Found | Percent H Calc'd. | Percent H Found | Percent N Calc'd. | Percent N Found | Percent S Calc'd. | Percent S Found |
|---|---|---|---|---|---|---|---|---|---|---|---|---|
| 2 | H | S | 81–2[b] | 95 | — | — | — | — | 13.58 | 13.51 | 31.09 | 31.38 |
| 3 | H | NH | 160–1[a] | 90 | 57.12 | 57.07 | 3.73 | 3.74 | 22.21 | 22.19 | 16.94 | 16.97 |

[a]Recrystallization from isopropyl alcohol.
[b]Recrystallization from heptane.

In accordance with the above procedure, 2-benzoxazolethioacetonitrile (Compound No. 1) was prepared by adding 8.4 g (0.11 mole) of chloroacetonitrile in one portion to a stirred solution containing 0.1 mole of 2-mercaptobenzoxazole, 6.6 g (0.1 mole) of 85% potassium hydroxide, 200 ml. of acetone and 10 ml. of water. An exothermic reaction set in causing a temperature rise from 25° to 50° C. The stirred reaction mixture was heated at reflux for six hours. After cooling to 5° C., 800 grams of ice water was added and stirring continued at 0°–10° C. for 30 minutes. The solid was collected by filtration, washed with water until neutral to litmus and air-dried at 25°–30° C. Compound No. 1 having the structure

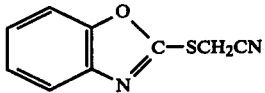

was obtained in 92% yield, m.p. 97°–98° C. from isopropyl alcohol.

Anal. Calc'd: C, 56.83; H, 3.18; N, 14.73; S, 16.86. Found: C, 56.80; H, 3.19; N, 14.70; S, 16.86.

Similarly, the compounds identified in Table I have been prepared.

To a stirred solution containing 0.2 mole of 2-mercaptobenzothiazole or 2-mercaptobenzimidazole, 13.2 grams (0.2 mole) of potassium hydroxide and 500 ml. of water, 15.2 grams (0.2 mole) of chloroacetonitrile was added in one portion. After stirring at 25°–30° C. for three hours, the solid was collected by filtration, washed with water until neutral to litmus and air-dried at 25°–30° C. The data are summarized in Table I.

In a similar manner, the compounds identified in Table II have been prepared.

To a stirred solution containing 0.2 mole of the appropriate mercaptan, 13.2 g (0.2 mole) of 85% potassium hydroxide, 200 ml. of dimethyl formamide and 20 ml. of water, 20.7 grams (0.2 mole) of 4-chlorobutyronitrile was added in one portion. The stirred reaction mixture was heated at 90°–100° C. for six hours and at 25°–30° C. for 18 hours.

To prepare Compound Nos. 4 and 5, 500 ml. of water and 600 ml. of ethyl ether were added and stirring continued at 25°–30° C. for 15 minutes. The separated ether layer was washed with water until neutral to litmus and dried over sodium sulfate. The ether was removed in vacuo at a maximum temperature of 80°–90° C. at 1–2 mm.

To prepare Compound Nos. 6 and 7, 800 grams of ice water was added and stirring continued at 10°–20° C. for 30 minutes. The solid was collected by filtration, washed with water until neutral to litmus and air-dried at 25°–30° C. The data are summarized in Table II.

Compound 8 was prepared using the procedure described for the preparation of compound Nos. 4 and 5 above, except that the stirred reaction mixture was heated at 90°–100° C. for twenty-four hours.

The data are summarized in Table II.

TABLE II

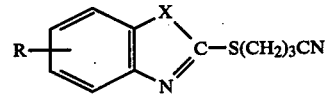

| Compound No. | R | X | m.p. °C. | Percent Yield | $N_D^{25}$ | Percent N Calc'd. | Percent N Found | Percent S Calc'd. | Percent S Found | Percent Cl Calc'd. | Percent Cl Found |
|---|---|---|---|---|---|---|---|---|---|---|---|
| 4 | H | S | amber liquid | 90 | 1.6405 | 11.96 | 11.85 | 27.37 | 27.16 | — | — |
| 5 | H | O | amber liquid | 94 | 1.5903 | 12.84 | 12.93 | 14.69 | 14.84 | — | — |
| 6 | H | NH | 137–8[a] | 83 | — | 19.34 | 19.43 | 14.76 | 14.87 | — | — |
| 7 | 5-Cl | S | 74–5[b] | 98 | — | 10.42 | 10.52 | 23.86 | 24.05 | 13.19 | 13.09 |
| 8 | 4-CH$_3$ | S | amber liquid | 97 | 1.6324 | 11.28 | 11.38 | 25.82 | 25.84 | — | — |

[a]Recrystallization from ethyl acetate.
[b]Recrystallization from heptane-isopropyl alcohol.

Compounds of Formula I wherein n is 4, 5 or 6 may be prepared according to the following procedure until neutral to litmus and air-dried at 25°-30° C. The data are summarized in Table III.

TABLE III

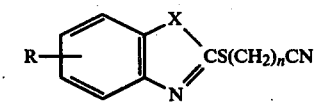

| Compound No. | R | X | n | m.p. °C. | $N_D^{25}$ | Percent Yield | Percent C Calc'd. | Found | Percent H Calc'd. | Found | Percent N Calc'd. | Found | Percent S Calc'd. | Found |
|---|---|---|---|---|---|---|---|---|---|---|---|---|---|---|
| 9 | H | S | 4 | 53-4 | — | 99 | 58.03 | 57.89 | 4.87 | 4.90 | 11.28 | 11.20 | 25.82 | 25.96 |
| 10 | H | O | 4 | amber liquid | 1.5812 | 94 | 62.04 | 61.86 | 5.21 | 5.27 | 12.06 | 12.04 | 13.80 | 13.73 |
| 11 | 5-Cl | S | 4 | 53-5 | — | 99 | 50.96 | 50.53 | 3.92 | 3.83 | 9.91 | 9.60 | 22.67 | 22.98 |
| 12 | H | NH | 4 | 130-2 | — | 91 | 62.31 | 62.26 | 5.66 | 5.72 | 18.17 | 18.10 | 13.86 | 13.91 |
| 13 | H | S | 6 | amber liquid | 1.6056 | 97 | 60.83 | 60.78 | 5.83 | 5.86 | 10.13 | 10.12 | 23.20 | 23.09 |
| 14 | H | O | 6 | amber liquid | 1.5641 | 88 | 64.59 | 64.36 | 6.19 | 6.25 | 10.76 | 10.73 | 12.32 | 12.25 |
| 15 | 5-Cl | S | 6 | 56-8 | — | 99 | 54.09 | 54.00 | 4.86 | 4.88 | 9.01 | 9.01 | 20.63 | 20.60 | which is illustrated by the reaction:

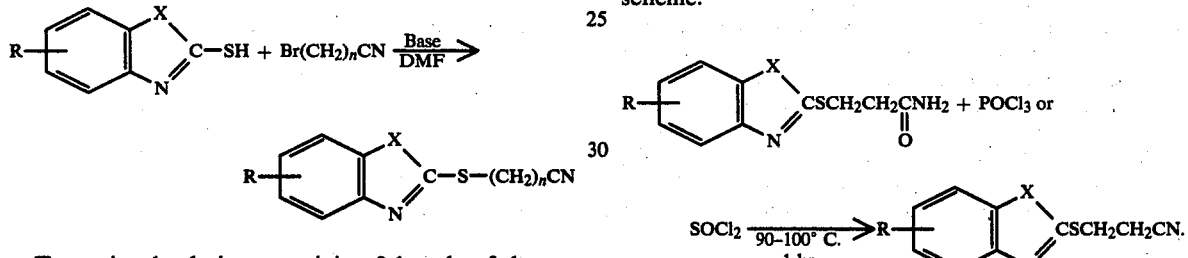

To a stirred solution containing 0.1 mole of the appropriate mercaptan, 6.6 g (0.1 mole) of 85% potassium hydroxide, 200 ml of dimethyl formamide and 10 ml of water, 0.11 mole of 5-bromovaleronitrile, 6-bromocaprolonitrile or 6-bromehexyl cyanide was added in one protion. The stirred reaction mixture was heated at 90°-100° C. for 48 hours.

To prepare Compound Number 10, 13 and 14, after cooling to 25° C., 500 ml of water and 600 ml of ethyl ether was added and stirring continued at 25°-30° C. for 15 minutes. The separated ether layer was washed with water until neutral to litmus and dried over sodium sulfate. The ether was removed in vacuo at a maximum temperature of 80°-90° C. at 1-2 mm.

To prepare Compound Numbers 9, 11, 12 and 15, after cooling to 5° C., 800 grams of ice water was added and stirring continued at 0°-10° C. for 30 minutes. The solid was collected by filtration, washed with water until neutral to litmus and air-dried at 25°-30° C. The data are summarized in Table III.

Compounds of Formula I wherein n is equal to 2 were prepared according to the following reaction scheme:

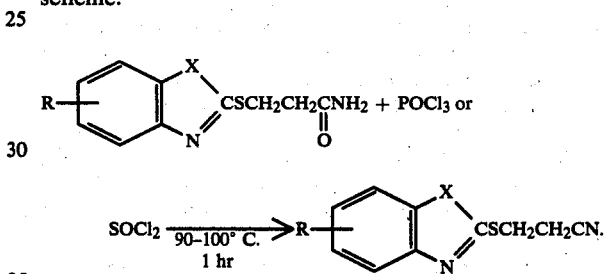

To a stirred solution at 90° C. containing 0.1 mol of the appropriate starting material in 100 ml of DMF, 0.12 mol of phosphorus oxychloride or thionyl chloride was added dropwise at 90°-100° C. over a 5 minute period. The stirred solution was heated at 90°-100° C. for one hour. For Compound No. 16 and Compound No. 17 after cooling to 5° C., 800 grams of ice water was added and stirring continued at 0°-10° C. for 30 minutes. The solid was collected by filtration, washed with water until neutral to litmus and air-dried at 25°-30° C. For Compound No. 18 after cooling to 5° C., 500 grams of ice water and 500 ml of ethyl ether were added and stirring continued at 25°-30° C. for 15 minutes. The separated ether layer was washed with water untril neutral to litmus and dried over sodium sulfate. The ether was removed *in vacuo* at a maximum temperature of 80°-90° C. for 1-2 minutes. The data are summarized in Table IV.

TABLE IV

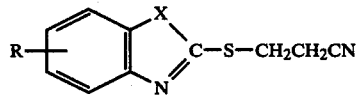

| Compound No. | Mol POCl₃ | SOCl₂ | R | X | Mp, °C. | % Yield | % C Calcd | Found | % H Calcd | Found | % Cl Calcd | Found | % N Calcd | Found | % S Calcd | Found |
|---|---|---|---|---|---|---|---|---|---|---|---|---|---|---|---|---|
| 16 | 0.12 | — | H | O | 46-7[a] | 86 | 58.80 | 58.53 | 3.95 | 4.01 | — | — | 13.72 | 13.65 | 15.70 | 15.81 |
|  | — | 0.12 |  |  | 45-7[a] | 84 | 58.80 | 58.66 | 3.95 | 4.00 | — | — | 13.72 | 13.67 | 15.70 | 15.73 |
| 17 | 0.12 | — | 5-Cl | S | 86-8[b] | 98 | 47.15 | 47.12 | 2.77 | 2.81 | 13.92 | 13.85 | 11.00 | 10.95 | 25.17 | 25.08 |
|  | — | 0.12 |  |  | 86-8[b] | 94 | 47.15 | 46.84 | 2.77 | 2.74 | 13.92 | 14.25 | 11.00 | 10.79 | 25.17 | 24.91 |
| 18 | 0.12 | — | H | S | Visc am- | 99 | 54.52 | 54.56 | 3.66 | 3.59 | — | — | 12.72 | 12.44 | 29.11 | 28.46 |

TABLE IV-continued

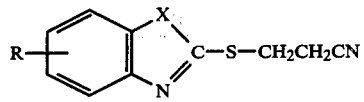

| Compound No. | Mol POCl3 | Mol SOCl2 | R | X | Mp, °C. | % Yield | % C Calcd | % C Found | % H Calcd | % H Found | % Cl Calcd | % Cl Found | % N Calcd | % N Found | % S Calcd | % S Found |
|---|---|---|---|---|---|---|---|---|---|---|---|---|---|---|---|---|
| | — | 0.12 | | | amber liquid Visc amber liquid | 95 | 54.52 | 54.03 | 3.66 | 3.64 | — | — | 12.72 | 12.25 | 29.11 | 29.55 |

[a] Recrystallization from heptane/isopropyl alcohol (2.5/1.0).
[b] Recrystallization from isopropyl alcohol To illustrate the variety of regulatory responses observed, the compounds of the invention were tested in accordance with the following procedure.

A number of soybean plants are grown from seeds in plastic pots in the greenhouse for a period of one week at which time the plants are thinned to one plant per pot. When the second trifoliate leaf is fully expanded, the plants are treated with a solution of the active ingredient in acetone and water. Aqueous Tween 20 is used as a surfactant.

When the fifth trifoliate leaf of the control is fully expanded, the treated plants are compared with the nontreated control plants and the observations recorded.

The following observations were made when soybeans were treated at the indicated rates with the compounds of the foregoing formula.

| Compound Number | Rate (kg/ha) | Observations |
|---|---|---|
| 4 | 2.8 | Stature reduction, inhibition of dry weight, slight leaf burn, leaf distortion, leaf alteration, altered canopy. |
| | 0.56 | No response. |
| | 0.112 | Increased dry weight. |
| 9 | 2.8 | Leaf alteration, inhibition of dry weight. |
| | 0.56 | No response. |
| | 0.112 | No response. |
| 10 | 2.8 | Increased dry weight. |
| | 0.56 | Increased dry weight. |
| | 0.112 | No response |
| 11 | 2.8 | Stature reduction, inhibition of dry weight, leaf inhibition. |
| | 0.56 | No response. |
| | 0.112 | Inhibition of dry weight. |
| 12 | 2.8 | Stature reduction, inhibition of dry weight, leaf alteration, leaf inhibition, leaf alteration new growth. |
| | 0.56 | Inhibition of dry weight. |
| | 0.112 | No response. |
| 13 | 2.8 | Inhibition of dry weight, leaf alteration, leaf alteration new growth, slight leaf burn. |
| | 0.56 | No response. |
| | 0.112 | No response. |
| 14 | 2.8 | Inhibition of dry weight, slight leaf burn, leaf alteration, leaf alteration new growth. |
| | 0.56 | Leaf alteration new growth. |
| | 0.112 | Inhibition of dry weight. |
| 16 | 2.8 | Stature reduction, leaf alteration, leaf inhibition, leaf alteration new growth, slight leaf burn. |
| | 0.56 | No response noted. |
| | 0.112 | No response noted. |
| 18 | 2.8 | Stature reduction, leaf inhibition, leaf distortion, leaf distortion new growth, severe leaf burn, inhibition of dry weight. |
| | 0.56 | No response noted. |
| | 0.112 | No response noted. |

The compounds of the invention were further tested as follows.

A number of soybean plants are grown from seeds in aluminum pans in the greenhouse for a period of approximately 1 week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. The composition formulated with acetone and Tween 20 as a surfactant is then applied to the pan of growing plants by overhead spray at a rate equivalent to the desired rate of active ingredient per acre. The treated pans, along with the control pans, are maintained in a greenhouse and watered from below on a sand bench and fertilized with a uniform portion of a water-soluble balanced fertilizer.

Two weeks after application of the chemical, the average height of the soybean plants in the treated pan is again measured as above and the difference in the average height before and 2 weeks after application represents the increase in the development of the treated pans. This development in growth of the treated plants is compared to the average increase in growth of the plants in the control pans during the same period of time. A variation of 25% or more in the development of at least two-thirds of the treated plants when compared to the development of the control plants demonstrates that the chemical is an effective plant regulant. Thus, a chemical is considered active when the treated plants manifest a decrease in growth of at least 25% less than that of the control plants, i.e., stature reduction, or an increase in growth in excess of 25% of that of the control plants, i.e., growth stimulation.

The following results and observations were made when the benzothiazolines of the invention were utilized as the active ingredient at several rates.

| Compound Number | Rate (kg/ha) | Observations |
| --- | --- | --- |
| 2 | 6.72 | Stature reduction, slight leaf burn, stimulation of axillary buds, inhibition of apical development. |
|   | 3.36 | Stature reduction, slight leaf burn, stimulation of axillary buds, inhibition of apical development. |
|   | 1.34 | No response. |
| 3 | 6.72 | Stature reduction, slight leaf burn, leaf alteration. |
|   | 3.36 | No response. |
| 5 | 6.72 | Slight leaf burn, leaf distortion, stimulation of axillary buds. |
| 6 | 6.72 | Slight leaf burn, leaf distortion. |
| 7 | 6.72 | No response. |
| 1 | 6.72 | Altered canopy, leaf alteration, stimulation of axillary buds. |
|   | 6.72 | Stature reduction, slight leaf burn, inhibition of apical development, stimulation of axillary buds. |
|   | 3.36 | Altered canopy, leaf alteration, stimulation of axillary buds. |
|   | 1.34 | Leaf alteration. |
| 4 | 6.72 | Stature reduction, slight leaf burn, defoliation. |
|   | 3.36 | Stature reduction, slight leaf burn, defoliation. |
|   | 1.34 | Stimulation of axillary buds, slight leaf burn. |

Further tests were conducted as follows.

Individual soybean plants are grown from seed in 6-inch pots containing a good grade of top soil. Two pots of 6-week old plants (5–6 trifoliate stage) are used for each application of the chemical. An overhead spray of an aqueous composition of the chemical is applied to the pots at an equivalent rate as indicated below. Two to four sets of plants which received no chemical application are included and serve as controls. All of the pots are maintained under good growing conditions and are watered and are fertilized with a uniform amount of water-soluble balanced fertilizer. Two weeks after the application of the chemical, the growth responses of the treated plants are compared with that of the control plants. The total height of the plant is measured to the tip of the terminal bud. A variation of 15% in the average total height of the treated plants, when compared to the average total height of the control plants, demonstrate that the chemical is an effective plant growth regulator. Observations made utilizing this procedure are summarized as follows.

| Compound Number | Rate (kg/ha) | Observations |
| --- | --- | --- |
| 4 | 2.8 | Leaf distortion, leaf alteration, delayed pod set, inhibited pod set. |
|   | 1.12 | Stature reduction, leaf alteration. |
|   | 0.56 | No response. |

From the above data, it can be seen that the compounds of the present invention are especially effective in reducing the stature of the soybean plant as well as altering the leaf morphology.

In practicing the plant growth regulating methods of this invention, the active ingredient can be used alone or in combination with a material referred to in the art as an adjuvant in liquid or solid form. The plant growth regulating compositions of this invention are prepared by admixing the active ingredient with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent, or emulsifying agent or any suitable combination of these.

When applying the active ingredient to leguminous plants, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful in applying the active ingredient to leguminous plants include, for example, Stoddard solvent, acetone, alcohols, glycols, ethyl acetate, benzene and the like. Such leguminous plant growth regulating compositions, particularly liquids and wettable powders, usually contain as a conditioning agent one or more surface-active agents in amounts sufficient to render a given composition readily dispersible in water or in oil. By the term "surface-active agent," it is understood that wetting agents, dispersing agents, suspending agents and emulsifying agents are included therein. Such surface-active agents are well known and reference is made to U.S. Pat. No. 2,547,724, columns 3 and 4, for detailed examples of the same.

Compositions of this invention generally contain from about 5 to 95 parts active ingredient, about 1 to 50 parts surface-active agent and about 4 to 94 parts solvent, all parts being by weight based on the total weight of the composition.

Desirable modification of leguminous plants may be achieved by applying the above-described plant regulants to the plant locus. The term "plant locus" is understood herein to include the plant growing medium, such as the soil, as well as the seeds, emerging seedlings, roots, stems, leaves, flowers, fruits or other plant parts.

The application of liquid and particulate solid compositions of the active ingredient can be carried out by conventional techniques utilizing, for example, spreaders, power dusters, boom and hand sprayers and spray dusters. The compositions can also be applied from airplanes as a dust or spray. If desired, application of the compositions of the invention to leguminous plants can be accomplished by incorporating the compositions in the soil or other media in the area where modification of the plants is desired.

In selecting the appropriate non-toxic rate of application of the active ingredient to leguminous plants, it will be recognized that precise rates will also be dependent upon the mode of application, such as soil incorporation, band application, pre-plant seed treatment, result desired and various other factors known to those skilled in the art. In applications to the soil habitat of germinant seeds, emerging seedlings, and established vegetation for the regulation of plant growth, the active ingredients are applied in amounts of from about 0.056 to 22.4 kilos/hectare. Foliar application is particularly advantageous and is preferred especially from about 0.112 to about 6.7 kilos/hectare.

Although this invention has been described with respect to specific modifications, the details thereof are not to be construed as limitations, for it will be apparent

What is claimed is:

1. A compound having the formula:

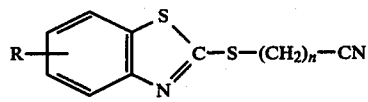

wherein R is hydrogen, halogen, or alkyl having 1 to 5 carbon atoms; n is equal to 1, 3, 4, 5, or 6.

2. A compound according to claim 1 wherein n is 3, 4 or 6.

3. A compound according to claim 3 wherein n is 3.

4. A compound according to claim 1 wherein R is hydrogen, chloro or methyl.

5. A compound according to claim 1 wherein said compound is

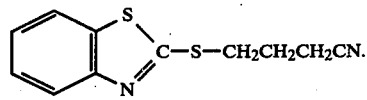

6. A compound according to claim 1 wherein said compound is

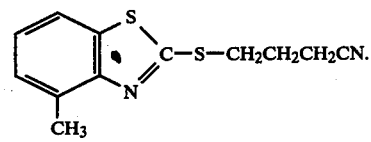

* * * * *